United States Patent
Taylor et al.

(10) Patent No.: US 9,849,247 B2
(45) Date of Patent: Dec. 26, 2017

(54) LOW DOSE PREFILLED DRUG DELIVERY DEVICE AND METHOD

(75) Inventors: Margaret Taylor, Groton, MA (US); James Bates, Sparta, NJ (US); Roman Tunkel, Burlington, MA (US); Jay Butterbrodt, North Andover, MA (US); Gary Searle, Norfolk, MA (US); Joshua Horvath, Sparta, NY (US); Keith Knapp, II, Warwick, NJ (US); Edward Gillen, Ridgewood, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 600 days.

(21) Appl. No.: 13/261,383

(22) PCT Filed: Jan. 31, 2011

(86) PCT No.: PCT/US2011/000174
§ 371 (c)(1),
(2), (4) Date: Sep. 14, 2012

(87) PCT Pub. No.: WO2011/094025
PCT Pub. Date: Aug. 4, 2011

(65) Prior Publication Data
US 2013/0006216 A1    Jan. 3, 2013

Related U.S. Application Data

(60) Provisional application No. 61/300,373, filed on Feb. 1, 2010.

(51) Int. Cl.
*A61M 5/24* (2006.01)
*A61M 5/32* (2006.01)
(Continued)

(52) U.S. Cl.
CPC ........ *A61M 5/2425* (2013.01); *A61M 5/2459* (2013.01); *A61M 5/3287* (2013.01);
(Continued)

(58) Field of Classification Search
CPC .... A61M 2005/005; A61M 2005/3208; A61M 5/31583; A61M 2005/3289; A61M 5/3287; A61M 5/3295; A61M 5/34
See application file for complete search history.

(56) References Cited

U.S. PATENT DOCUMENTS

| 2,667,165 A | 1/1954 | Smith |
| 3,675,651 A * | 7/1972 | Meyer ................... A61M 5/204 604/144 |

(Continued)

FOREIGN PATENT DOCUMENTS

| AU | 8757382 A | 3/1984 |
| EP | 0400216 A1 | 12/1990 |

(Continued)

OTHER PUBLICATIONS

Gerich, John E., Is Reduced First-Phase Insulin Release the Earliest Detectable Abnormality in Individuals Destined to Develop Type 2 Diabetes?, Diabetes, vol. 51, Supplement 1, S117-S121, Feb. 2002.
(Continued)

*Primary Examiner* — Imani Hayman
*Assistant Examiner* — Matthew A Engel
(74) *Attorney, Agent, or Firm* — Dickinson Wright PLLC

(57) ABSTRACT

A drug delivery device (100) for administering a low dose of a medicament includes a housing (111) and a drug reservoir (101) disposed in the housing (111). A needle (135) is connected to the drug reservoir (101). A pressure applying member (113) is movably connected to the housing (111) and is movable between first and second positions. The pressure applying member (113) does not apply pressure to
(Continued)

the drug reservoir (101) in the first position and applies pressure to the drug reservoir (101) in the second position to dispense medicament stored in the drug reservoir (101). A method of administering a low dose of insulin to simulate a first-phase insulin response of a pancreas is also disclosed.

7 Claims, 16 Drawing Sheets

(51) Int. Cl.
    *A61M 5/42*     (2006.01)
    *A61M 5/00*     (2006.01)
    *A61M 5/20*     (2006.01)

(52) U.S. Cl.
    CPC ....... *A61M 5/425* (2013.01); *A61M 2005/005* (2013.01); *A61M 2005/206* (2013.01)

(56) References Cited

U.S. PATENT DOCUMENTS

| | | | |
|---|---|---|---|
| 3,953,771 A * | 4/1976 | Bremstahler | 361/293 |
| 4,013,073 A | 3/1977 | Cunningham | |
| 4,282,986 A | 8/1981 | af Ekenstam | |
| 4,518,384 A * | 5/1985 | Tarello | A61M 5/20 604/61 |
| 4,883,473 A | 11/1989 | Thomas | |
| 4,955,871 A | 9/1990 | Thomas | |
| 5,019,048 A | 5/1991 | Margolin | |
| 5,020,395 A * | 6/1991 | Mackey | B67B 7/08 141/19 |
| 5,147,328 A | 9/1992 | Dragosits | |
| 5,222,948 A | 6/1993 | Austin | |
| 5,829,589 A * | 11/1998 | Nguyen et al. | 206/366 |
| 5,957,895 A | 9/1999 | Sage | |
| 6,776,776 B2 | 8/2004 | Alchas | |
| 6,843,781 B2 | 1/2005 | Alchas | |
| 8,579,861 B2* | 11/2013 | Radmer et al. | 604/173 |
| 8,690,836 B2* | 4/2014 | Mathews et al. | 604/185 |
| 8,845,549 B2* | 9/2014 | Freeman et al. | 600/583 |
| 8,876,780 B2* | 11/2014 | Bruehwiler et al. | 604/198 |
| 2002/0020646 A1* | 2/2002 | Groth et al. | 206/366 |
| 2002/0177808 A1* | 11/2002 | Carmel | 604/124 |
| 2003/0040715 A1* | 2/2003 | D'Antonio et al. | 604/187 |
| 2004/0054326 A1* | 3/2004 | Hommann et al. | 604/131 |
| 2004/0092875 A1 | 5/2004 | Kochamba | |
| 2005/0165358 A1 | 7/2005 | Yeshurun et al. | |
| 2006/0293722 A1 | 12/2006 | Slatkine | |
| 2007/0156096 A1 | 7/2007 | Sonoda | |
| 2007/0173741 A1* | 7/2007 | Deshmukh et al. | 600/583 |
| 2007/0191780 A1* | 8/2007 | Modi | 604/187 |
| 2007/0233001 A1* | 10/2007 | Burroughs et al. | 604/131 |
| 2008/0051714 A1* | 2/2008 | Moberg et al. | 604/135 |
| 2009/0082727 A1* | 3/2009 | Moeller et al. | 604/132 |
| 2009/0209883 A1* | 8/2009 | Higgins et al. | 600/575 |
| 2010/0137695 A1* | 6/2010 | Yodfat | A61B 5/6849 600/345 |
| 2010/0179473 A1* | 7/2010 | Genosar | 604/70 |
| 2011/0022001 A1* | 1/2011 | Wei | 604/198 |
| 2011/0054285 A1* | 3/2011 | Searle et al. | 600/365 |
| 2011/0160674 A1* | 6/2011 | Holmes et al. | 604/192 |
| 2011/0160675 A1* | 6/2011 | Ruan et al. | 604/198 |
| 2011/0218497 A1* | 9/2011 | Assaf | 604/173 |
| 2012/0041381 A1* | 2/2012 | Raj et al. | 604/192 |
| 2012/0136310 A1* | 5/2012 | Kadamus et al. | 604/164.04 |
| 2012/0179113 A1* | 7/2012 | Yokota et al. | 604/239 |
| 2012/0191046 A1* | 7/2012 | Larsen et al. | 604/192 |
| 2013/0006216 A1* | 1/2013 | Taylor et al. | 604/506 |
| 2013/0041322 A1* | 2/2013 | Holmqvist | 604/189 |

FOREIGN PATENT DOCUMENTS

| | | |
|---|---|---|
| JP | S5695058 A | 8/1981 |
| JP | 2001-212231 A | 8/2001 |
| JP | 2005-087520 A | 4/2005 |
| JP | 2006-122712 A | 5/2006 |
| JP | 2007-534384 A | 11/2007 |
| JP | 2009-526575 A | 7/2009 |
| NL | 2000986 C2 | 5/2009 |
| WO | 03041763 A2 | 5/2003 |
| WO | 2004004803 A2 | 1/2004 |

OTHER PUBLICATIONS

European Search Report issued in Application No. 11737416.5-1662 dated Aug. 18, 2014.
Chinese Office Action dated Dec. 11, 2015 that issued in counterpart Patent Application No. 201180013049.5, ncluding English translation.
Japanese Office Action dated Dec. 1, 2015 that issued in corresponding Patent Application No. 2015-024605, including English translation.

* cited by examiner

LOW DOSE PREFILLED DRUG DELIVERY DEVICE AND METHOD

CROSS REFERENCE TO RELATED APPLICATION

This application claims the benefit under 35 U.S.C. §119 (e) of U.S. Provisional Application Ser. No. 61/300,373, filed Feb. 1, 2010, the entire content of which is hereby incorporated by reference.

FIELD OF THE INVENTION

The present invention relates to a pre-filled drug delivery device. More particularly, the present invention generally relates to a pre-filled drug delivery device that can facilitate an intradermal or subcutaneous injection. Still more particularly, the present invention provides a pre-filled insulin delivery device for delivering only a small insulin dose intended to replace the first-phase insulin response of a normal human pancreas.

BACKGROUND OF THE INVENTION

The release of insulin by a normal human pancreas in response to elevated glucose levels is known to consist of two phases. The first phase consists of a rapid increase in plasma insulin levels, reaching a maximum within a few minutes of the hyperglycemic stimulus. Plasma insulin levels decrease sharply after the first phase of insulin secretion, and a second, more gradual peak in plasma insulin levels (the second phase) is observed several hours later. A reduction in the first phase of insulin secretion by the pancreas is the earliest detectable abnormality in patients destined to develop type 2 diabetes. J. E. Gerich, *Diabetes*, Vol. 51, Supplement 1, February 2002, S117-S121, the entirety of which is hereby incorporated by reference. Accordingly, a need exists for a drug delivery device that supplies the missing first phase of insulin to a patient with diminished first-phase insulin release.

Insulin appears to be more readily absorbed when injected intradermally because of the high degree of vascularity in the intradermal layer. Such quick absorption of injected insulin by the body is beneficial when compensating for diminished first-phase insulin release at mealtime. Accordingly, a need also exists for a drug delivery device that supplies a replacement for first-phase insulin intradermally.

No existing drug delivery device provides only a first-phase insulin dose. Accordingly, a user must set the dose prior to making the injection, which could lead to dose inaccuracies. Accordingly, a need also exists for a drug delivery device that supplies only first-phase insulin without the need to set a dose.

Existing single-use prefilled disposable drug delivery devices, such as that disclosed in U.S. Pat. No. 4,955,871 to Thomas, issued Sep. 11, 1990, are not able to generate the high pressures associated with intradermal injections. A user can generate an injection pressure of approximately 20-30 psi with existing single-use disposable prefilled drug delivery devices. However, intradermal injections require an injection pressure of at least 200 psi. Therefore, a need exists for a pre-filled drug delivery device that generates an injection pressure sufficient for an intradermal injection.

SUMMARY OF THE INVENTION

In accordance with an aspect of the present invention, a drug delivery device supplies a small dose of rapidly absorbed insulin to a patient to compensate for reduced first-phase insulin release. Preferably, the drug delivery device supplies the first-phase replacement insulin dose intradermally.

The drug delivery device includes a drug reservoir, a hub assembly, which includes a needle, connected to the drug reservoir, and a mechanical device to apply pressure to the drug reservoir during the injection sufficient to overcome the back pressure associated with an intradermal injection. The drug reservoir preferably has a maximum capacity between 1 and 15 units (10 and 150 microliters), inclusive, of insulin, thereby providing a small, fast-acting dose of insulin to simulate first-phase insulin response when administered immediately prior to a meal. This first-phase insulin response is responsible for attenuation of glucose production in the liver and may have other advantages, including but not limited to improved glycemic control and substantially avoiding hyperinsulinemia.

More generally, the foregoing objectives are attained by a drug delivery device that administers a low dose of a medicament and includes a housing and a drug reservoir disposed in the housing. A needle is connected to the drug reservoir. A pressure applying member is movably connected to the housing and movable between first and second positions. The pressure applying member does not apply pressure to the drug reservoir in the first position and applies pressure to the drug reservoir in the second position to dispense medicament stored in the drug reservoir.

The foregoing objectives are also attained by a drug delivery device that administer a low dose of a medicament and includes a rigid member and first and second flexible portions connected to the rigid member. A drug reservoir containing a medicament is disposed in the first flexible portion. A needle is connected to the drug reservoir. A first pressure is applied to the second flexible portion to create a vacuum before contacting the second flexible portion with a patient's skin. A second pressure is applied to the first flexible portion to dispense the medicament after contacting the second flexible portion with the patient's skin and releasing the first pressure on the second flexible portion.

The foregoing objectives are also attained by a method of administering a low insulin dose. An injection site is penetrated with a needle of a pre-filled drug delivery device. Pressure is applied to the pre-filled drug delivery device to administer a first-phase insulin dose to simulate a first-phase insulin response of a pancreas.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENTS

Figure 1:
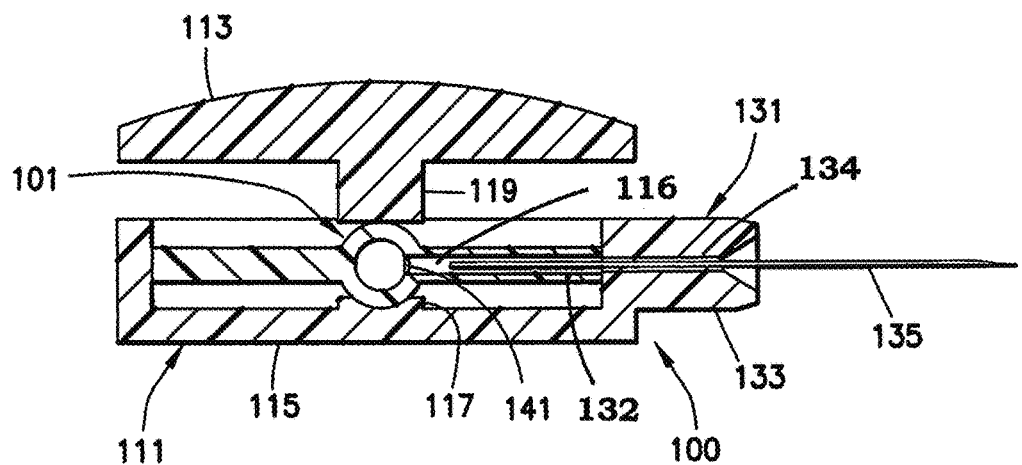
FIG. 1 is an elevational view in cross-section of a pre-filled drug delivery reservoir in a drug delivery device for administering a low dose of a medicament.

A low dose, pre-filled drug delivery device in accordance with exemplary embodiments of the present invention includes a drug reservoir containing a medicament, a hub assembly that includes a needle, and a mechanical device (pressure applying member) to apply pressure to the drug reservoir such that the medicament can be injected. Preferably, the medicament is insulin and the drug delivery device is used to inject insulin immediately prior to a meal to simulate first-phase insulin response. Immediately prior to a meal is defined to be no more than 5 minutes before the meal. By providing a small drug reservoir and the mechanical device, the drug delivery device is adapted to deliver a small, high pressure dose of the medicament. The reduced number of components of the drug delivery device reduces the cost and complexity of the drug delivery device. The small dose size also reduces the importance of dose accuracy, as well as reducing the frequency with which a user must monitor his or her glucose level. The drug delivery device can be designed for either subcutaneous or intradermal delivery of the medicament. Preferably, the medicament is injected intradermally to obtain a faster response in the body. Injecting intradermally increases the bioavailability of the injected medicament relative to subcutaneous or oral administration of the medicament.

To prevent an accidental needle stick, a drug delivery device can be provided with a needle safety feature, such as a shield. The drug delivery device according to exemplary embodiments of the present invention can be used for subcutaneous and intradermal injections. To control the injection length of the needle, the drug delivery device can include an injection length limiting device, thereby ensuring an intradermal injection. The preferred injection length for an intradermal needle is between approximately 0.5-3 mm, inclusive, and preferably between approximately between 1.5-2 mm, inclusive.

As shown in FIGS. 1-28, various mechanical devices (pressure applying members) can be used to develop the high pressure required for an intradermal injection. Some of the mechanical devices include, but are not limited to, a pair of gears or rollers that compress the drug delivery reservoir in a space between the gears or rollers, a second pressurized chamber within the device that supplies the pressure required for injection or priming, a piezoelectric film that deflects under electrical voltage, and a pre-tensioned spring as part of a mechanical force multiplier. Alternatively, a chemical reaction, such as a binary gas generator, low order explosive, or osmotic pressure gradient can be used to develop the required high pressure for an intradermal injection. In the case where the drug being administered is insulin, the drug delivery reservoir of each of the disclosed embodiments preferably has a maximum capacity of between 1 and 15 units, inclusive, of U-100 insulin (10 to 150 microliters) to provide a first-phase replacement insulin dose.

Figure 2:
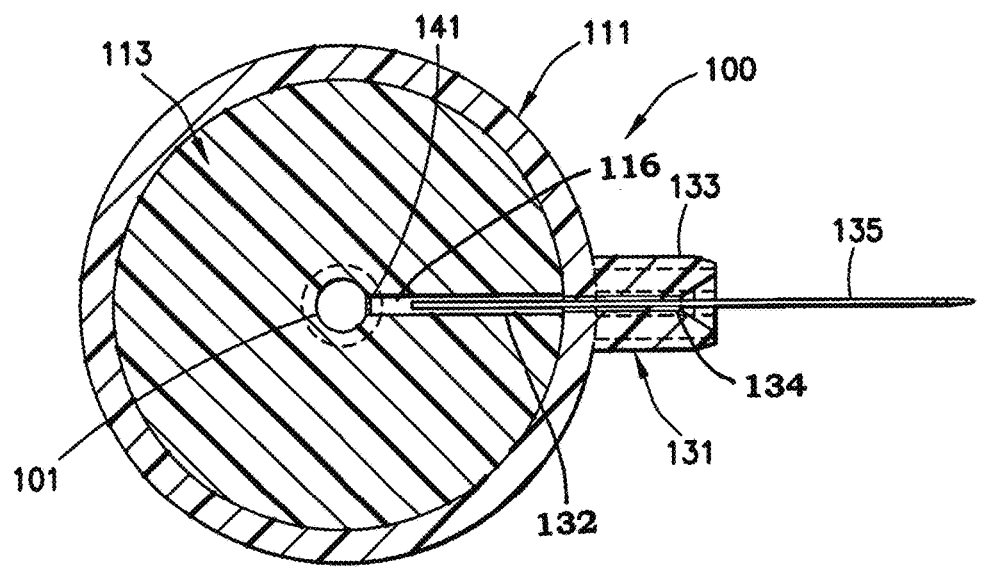
FIG. 2 is a top plan view of the drug delivery device of FIG. 1.

As shown in FIGS. 1 and 2, the drug delivery device 100 includes a drug reservoir 101 disposed in a plastic housing assembly 111. The housing assembly includes an upper housing 113 and a lower housing 115. The drug reservoir 101 is disposed on a piston 117 disposed in the lower housing 115. A corresponding piston 119 is disposed in the upper housing 113. A hub assembly 131, including a hub 133 and a needle 135, is connected to the housing assembly 111. As shown in FIG. 2, the hub assembly 131 is connected to the housing assembly 111 such that the needle 135 is in fluid communication with the drug reservoir 101 when a seal 141 in the drug reservoir is ruptured. The seal 141 is preferably a thin layer of plastic. The drug reservoir 101 includes an outlet passage 132 extending between the seal 141 and a fluid outlet channel 134 in the hub 133. Pressing downwardly on the upper housing 113 exerts a high pressure on the drug reservoir 101, thereby rupturing the seal 141 in the drug reservoir 101 and administering the medicament stored in the drug reservoir to the patient with high pressure through the needle 135. As shown in FIGS. 1 and 2, a gap 116 is formed between the seal 141 and the end of needle 135 before and after a dispensing pressure is applied to drug reservoir 101.

Figure 3:
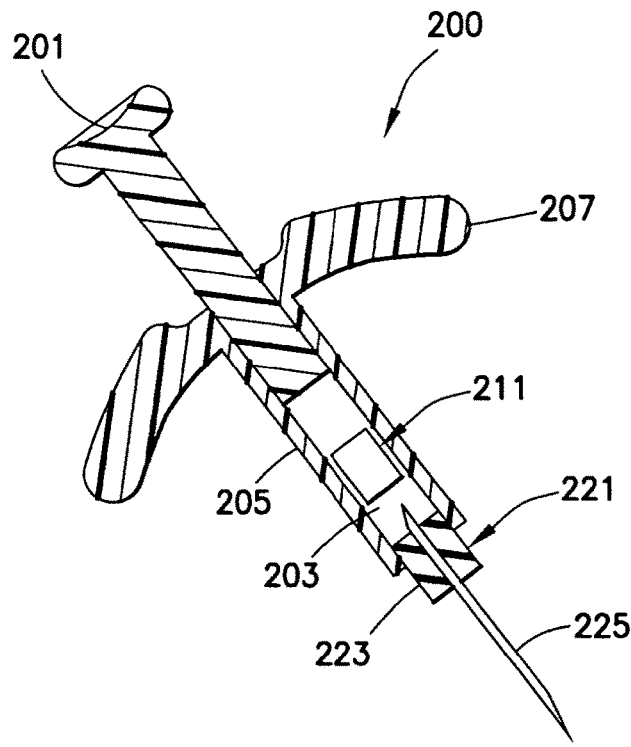
FIG. 3 is an elevational view in cross-section of a syringe having a pre-filled drug delivery reservoir for administering a low dose of a medicament.

As shown in FIG. 3, the drug delivery device 200 is a syringe-type drug delivery device. A plunger 201 is movably disposed within a channel 203 of a housing assembly 205. A drug reservoir 211 containing a medicament is disposed within the channel 203. A hub assembly 221, including a hub 223 and a double-ended needle 225, is connected to the housing assembly 205. The hub assembly 221 is connected to the housing assembly such that the needle 225 is in fluid communication with the drug reservoir 211 when the drug reservoir is ruptured. Finger grips 207 extend outwardly from the housing assembly 205, thereby allowing a user to generate a high pressure on the drug reservoir 211 during an injection. Pushing downwardly on the plunger 201 breaks the drug reservoir 211, thereby administering the medicament stored in the drug reservoir to the patient with high pressure through the needle 225.

Figure 4:
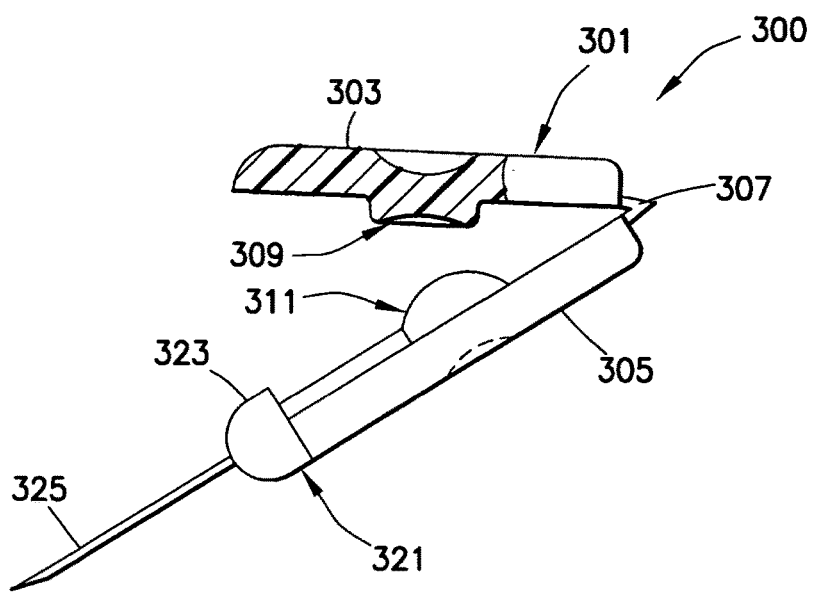
FIG. 4 is an elevational view of a pre-filled drug delivery reservoir in a side-hinged drug delivery device for administering a low dose of a medicament.

As shown in FIG. 4, the drug delivery device 300 includes a housing assembly 301 having a first housing 303 connected to a second housing 305 by a hinge 307. Preferably, the hinge 307 is a living hinge. A piston 309 is disposed in the first housing 303 for engaging a drug reservoir 311 disposed in the second housing 305. A hub assembly 321, including a hub 323 and a needle 325, is connected to the housing assembly 301. The hub assembly 321 is connected to the housing assembly 301 such that the needle 325 is in fluid communication with the drug reservoir 311 when the drug reservoir is ruptured. Closing the first housing 303 on the second housing 305 generates a mechanical advantage through the hinge 307 to compress and rupture the drug reservoir 311 and administer the medicament through the needle 325. Preferably, the piston 309 is a small diameter cylinder. The hinge 307 allows the lever arm (first housing 303) to increase pressure along with the small diameter of the piston 309 to create the high pressure required for an intradermal injection. A longitudinal axis of the needle 325 is substantially perpendicular to a direction in which force is applied on the drug reservoir 311 by a user during an injection.

Figure 5:
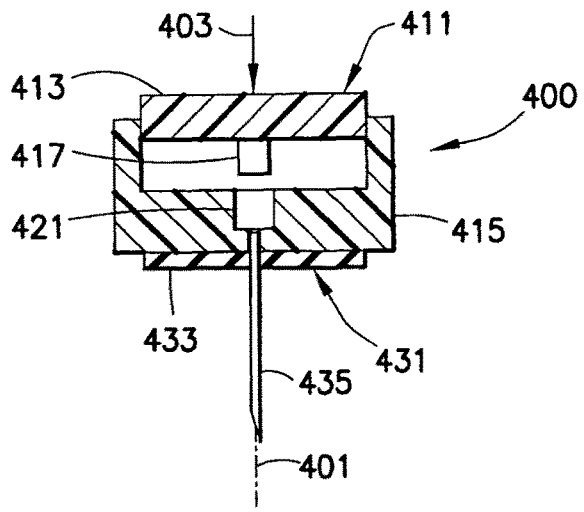
FIG. 5 is an elevational view in cross-section of a pre-filled drug delivery reservoir in a drug delivery device for administering a low dose of a medicament in which the needle axis is substantially parallel to an axis in which force is applied to a piston.
Figure 6:
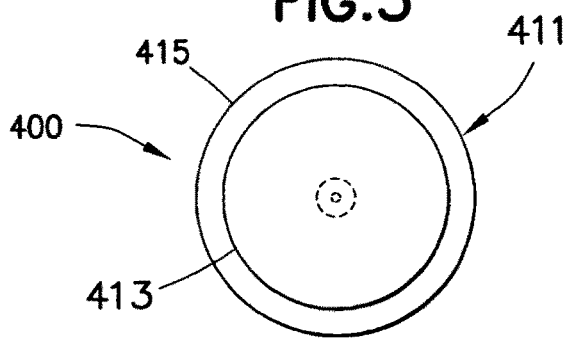
FIG. 6 is a top view of the drug delivery device of FIG. 5.

As shown in FIGS. 5 and 6, a drug delivery device 400 has a needle axis 401 that is substantially parallel to the direction in which force 403 is applied by the user during an injection. A housing assembly 411 includes an upper housing 413 and a lower housing 415. The upper housing 413 has a piston 417 disposed on a lower surface thereof and is movable through the lower housing 415. Preferably, the piston 417 has a small diameter. A drug reservoir 421 is disposed in the lower housing 415. A hub assembly 431, including a hub 433 and a needle 435, is connected to the housing assembly 411. The hub assembly 431 is connected to the housing assembly 411 such that the needle 435 is in fluid communication with the drug reservoir 421 when the drug reservoir is compressed. The user pushes downwardly on the upper housing 413, thereby moving the upper housing through the lower housing 415 such that the piston 417 compresses the drug reservoir 421 and ruptures the seal, thereby administering the medicament through the needle 435. A high pressure is generated that is sufficient for an intradermal injection. The drug delivery device 400 may include locking tabs to confirm the upper housing 413 is fully depressed and the entire dose of the drug reservoir 421 is delivered.

Figure 7:
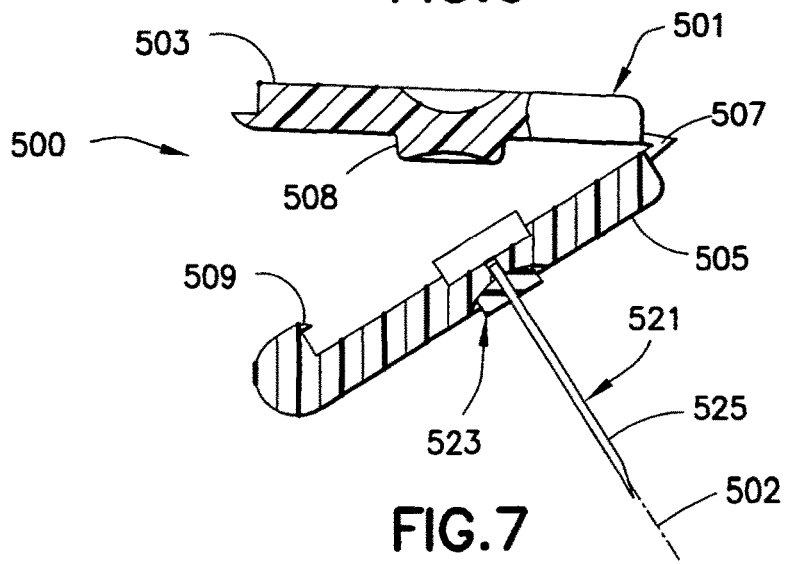
FIG. 7 is an elevational view of a pre-filled drug delivery reservoir in a side-hinged drug delivery device for administering a low dose of a medicament in which force is applied to the reservoir in a direction substantially parallel to the needle axis.

As shown in FIG. 7, a drug delivery device 500 is similar to the drug delivery device 400 of FIGS. 5 and 6, but the high pressure is generated by a hinge 507. The drug delivery device 500 has a needle axis 502 that is substantially parallel to the direction in which force is applied by the user on the drug reservoir 511 during an injection. A housing assembly 501 includes an upper housing 503 and a lower housing 505. The upper housing 503 has a piston 508 disposed on a lower surface thereof and is connected by a hinge 507 to be movable with respect to the lower housing 505. Preferably, the piston 508 has a small diameter. A drug reservoir 511 is disposed in the lower housing 505. A hub assembly 521, including a hub 523 and a needle 525, is connected to the housing assembly 501. The hub assembly 521 is connected to the housing assembly 501 such that the needle 525 is in fluid communication with the drug reservoir 511. The user rotates the upper housing 503 about the hinge 507, thereby moving the upper housing toward the lower housing 505 such that the piston 508 compresses the drug reservoir 511 and generates a high pressure sufficient for an intradermal injection. The drug delivery device 500 may include a locking tab 509 to confirm the upper housing 503 is fully depressed and the entire dose of the drug reservoir 511 is delivered. Additionally, the locking tab 509 prevents the upper housing 503 from being opened and the drug delivery device 500 from being reused.

Figure 8:
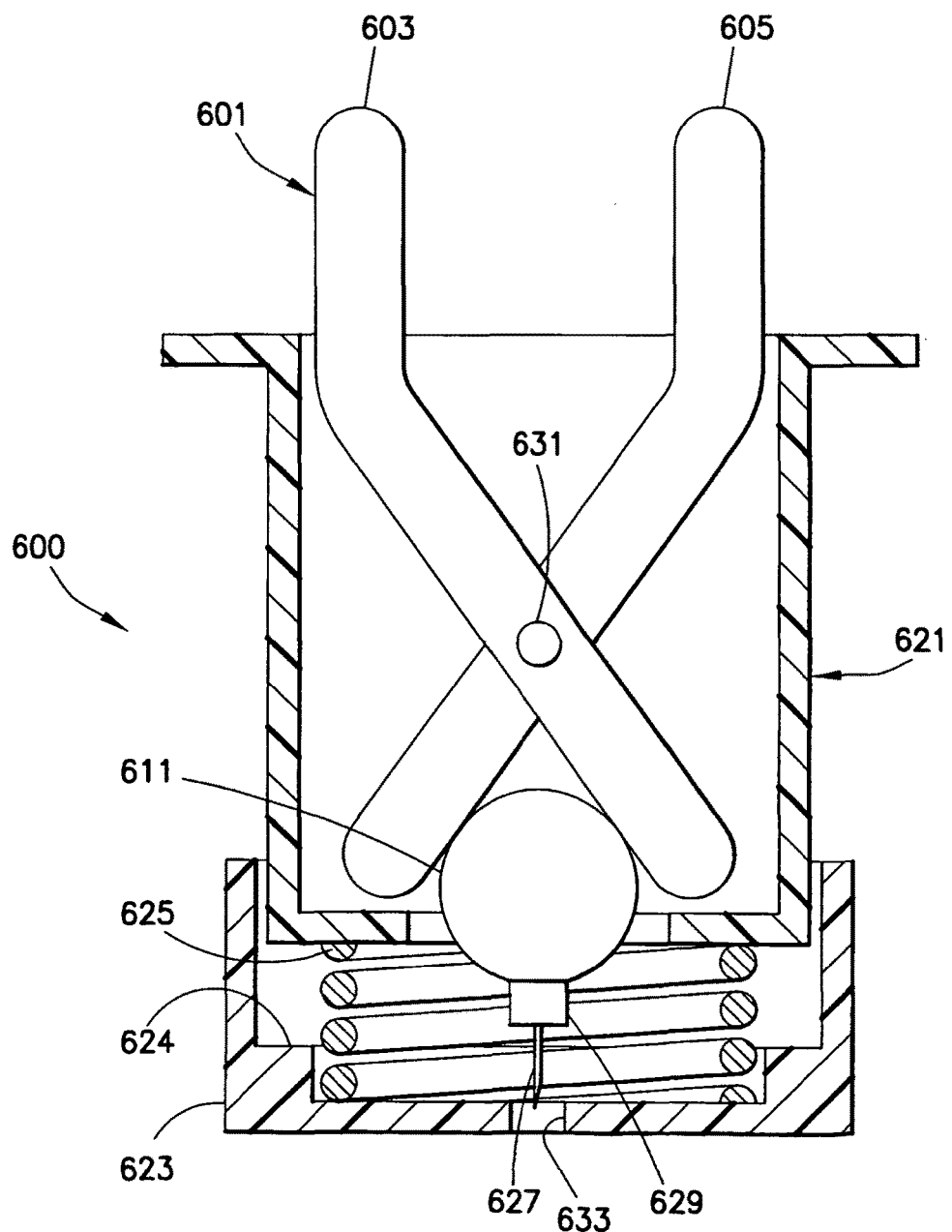
FIG. 8 is an elevational view in partial cross-section of a pre-filled drug delivery reservoir in a drug delivery device for administering a low dose of a medicament having a scissor-actuated injection mechanism.

A drug delivery device 600, as shown in FIG. 8, includes a scissor-actuated injection mechanism 601 to administer medicament stored in the drug reservoir 611. The scissor-actuated injection mechanism includes a first leg 603 and a second leg 605 movably connected by a pin 631. The drug reservoir 611 is disposed between ends of the first and second legs 603 and 605 within a housing assembly 621. A safety shield 623 is connected to the housing assembly 621. A spring 625 is disposed between the safety shield 623 and the housing assembly 621. A hub 629 is connected to the drug reservoir 611 such that the needle 627 is in fluid communication with the drug reservoir 611 when the seal of the drug reservoir is ruptured. The drug delivery device 600 is placed at an injection site and the housing is pushed downwardly to overcome the spring 625, thereby exposing the needle 627 through an opening 633 in the safety shield such that the needle 627 can be inserted in a patient's skin. Shoulders 624 of the safety shield 623 limit the insertion depth of the needle 627. The scissor-actuated injection mechanism 601 is then squeezed, thereby closing the ends of the legs 603 and 605 and compressing the drug reservoir 611 and rupturing its seal, thereby administering the medicament through the needle 627 with high pressure.

Figure 9:
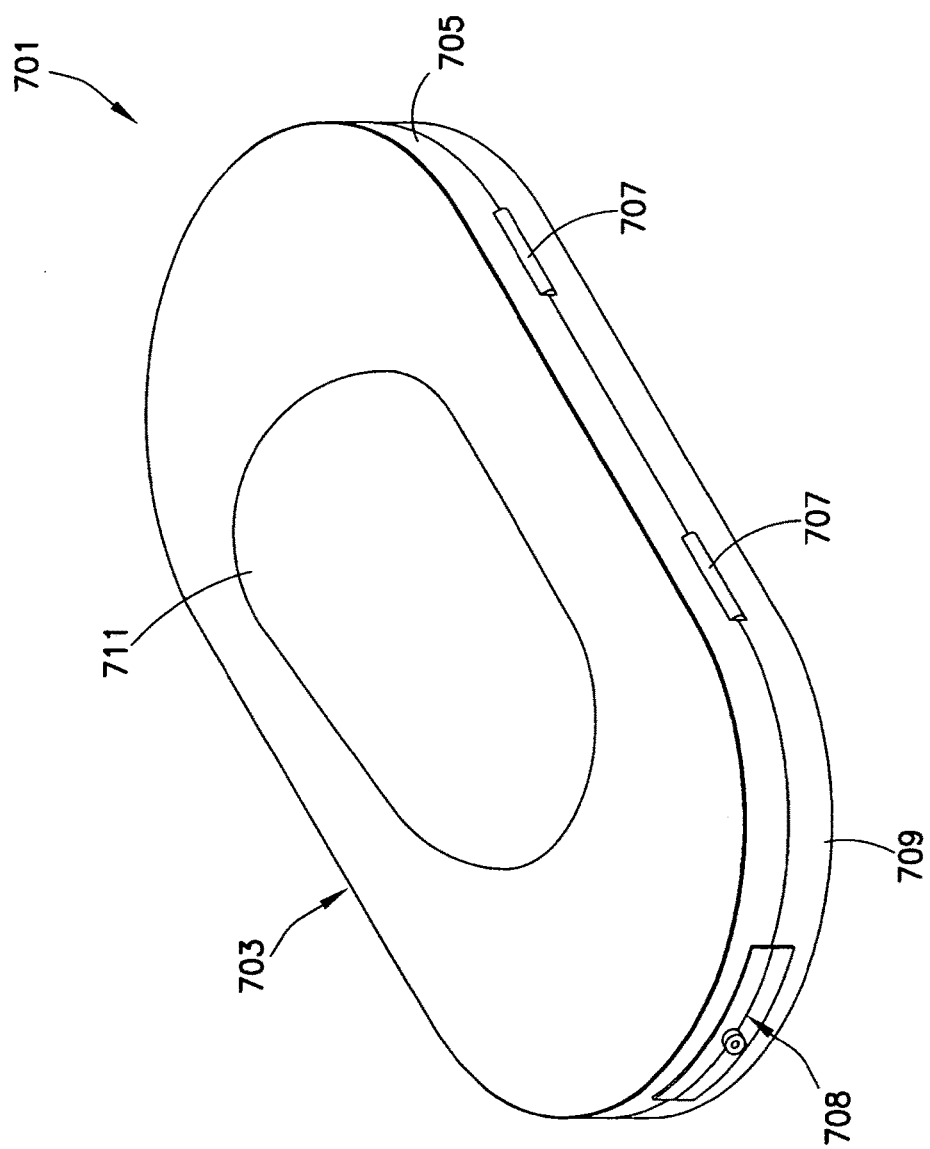
FIG. 9 is a perspective view of a housing of a drug delivery device for administering a low dose of a medicament.

A drug delivery device or drug dispensing kit 701 is shown in FIG. 9. The housing assembly 703 has a first housing 705 connected by hinges 707 to a second housing 709. Preferably, the housing assembly 703 is a hinged clamshell. An actuator 711 is integrally formed with the housing assembly 703. An opening 708 is formed in the housing assembly 703 through which the needle protrudes for an injection. Pressing the actuator 711 applies pressure to the drug reservoir disposed within the housing assembly 703 to compress the drug reservoir and rupture a seal in the fluid path, thereby administering the medicament to the user through the needle.

Figure 10:
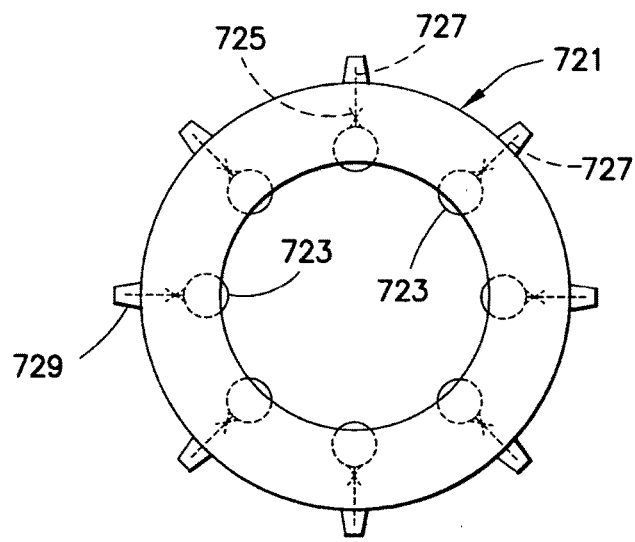
FIG. 10 is a top plan view of a medicament assembly having a plurality of pre-filled drug delivery reservoirs.
Figure 11:
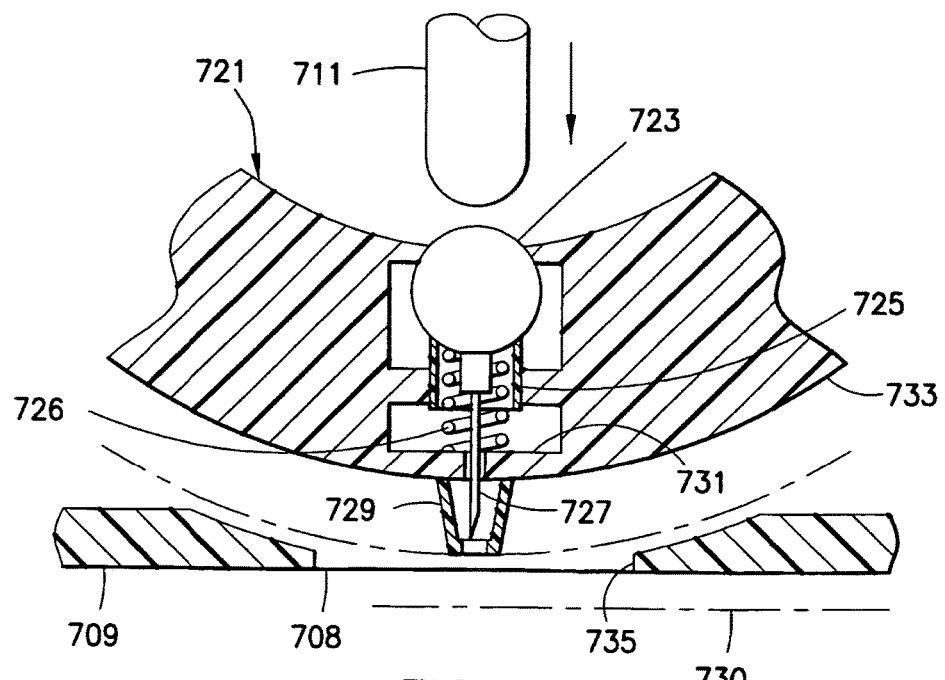
FIG. 11 is an elevational view in partial cross-section of the housing of FIG. 9 in which a medicament assembly of FIG. 10 is inserted.
Figure 12:
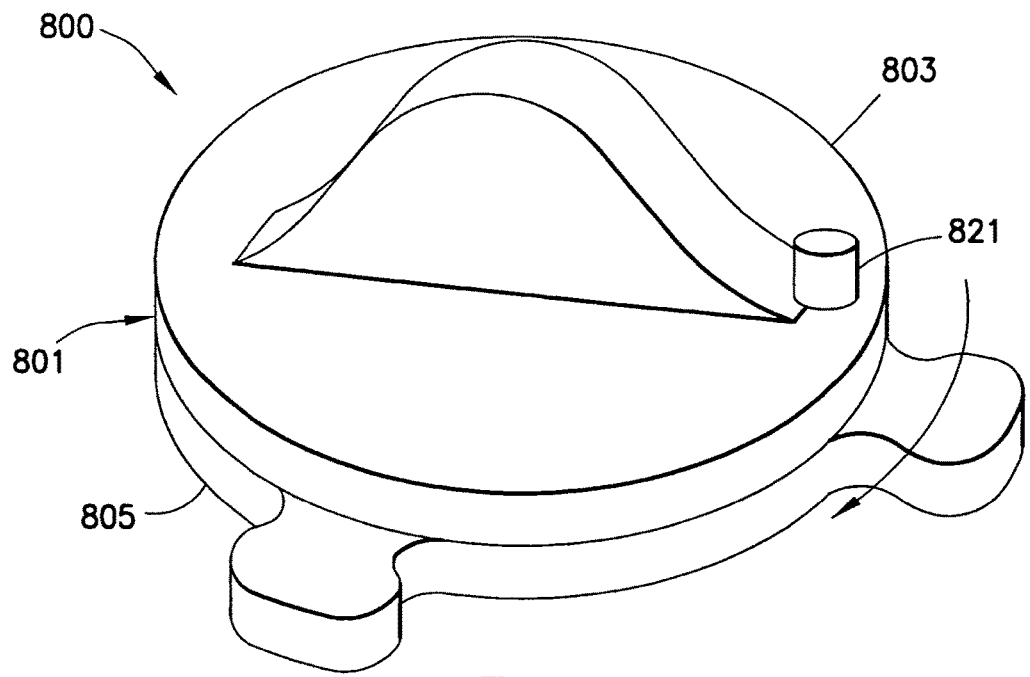
FIG. 12 is a perspective view of a housing assembly of a drug delivery device for administering a low dose of a medicament.

A dose or medicament wheel 721, as shown in FIGS. 10 and 11, may be disposed within the drug dispensing kit 701 of FIG. 9. The wheel 721 includes a plurality of drug reservoirs 723, each of which includes a hub 725 through which a needle 727 is connected in fluid communication with the drug reservoir 723 when the drug reservoir seal is ruptured. Preferably, the hub 725 includes a spring 726 disposed between a surface 731 of the dose wheel 721 and the drug reservoir 723. A safety shield 729 engages an outer surface 733 of the dose wheel 721, thereby preventing movement of the needle 727. When the safety shield 729 is removed, the spring expands to inject the needle 727 at an injection site. The dashed line 730 indicates the position to which the needle 727 is moved through an opening 735 in the drug dispensing kit 701 when the safety shield 729 is removed. The actuator 711 is then depressed, which causes the drug reservoir to be compressed and its seal ruptured, thereby administering the medicament through the needle 727 at a high pressure. The safety shield 729 is then reconnected to the hub 725, thereby causing the needle 727 to retract. The dose wheel 721 is then rotated for the next injection. After all the drug reservoirs 723 have been emptied, the dose wheel 721 is properly disposed of and a new dose wheel 721 is disposed in the drug dispensing kit 701. When the medicament being administered is insulin, each of the drug reservoirs 723 preferably has a maximum capacity of between 1 and 15 units, inclusive, of U-100 insulin (approximately 10 to 150 microliters) to provide a first-phase replacement insulin dose.

A drug delivery device 800, as shown in FIGS. 12-16, includes a housing assembly 801 having a cover 803 and a base 805. An opening 806 in the base 805 is adapted to receive the hub assembly 811. The hub assembly 811 includes a hub 813 to which a drug reservoir 815 and a needle 817 are connected. The drug reservoir 815 is disposed within the hub 813, which preferably has a luer lock for connecting to the base 805. A safety shield 819 is connected to the hub 813 to cover the patient end of the needle 817 and prevent accidental needle sticks. The needle 817 preferably has a depth below the lower surface 807 of the base 805 of approximately 1.5 mm, which is preferable for an intradermal injection.

Figure 13:
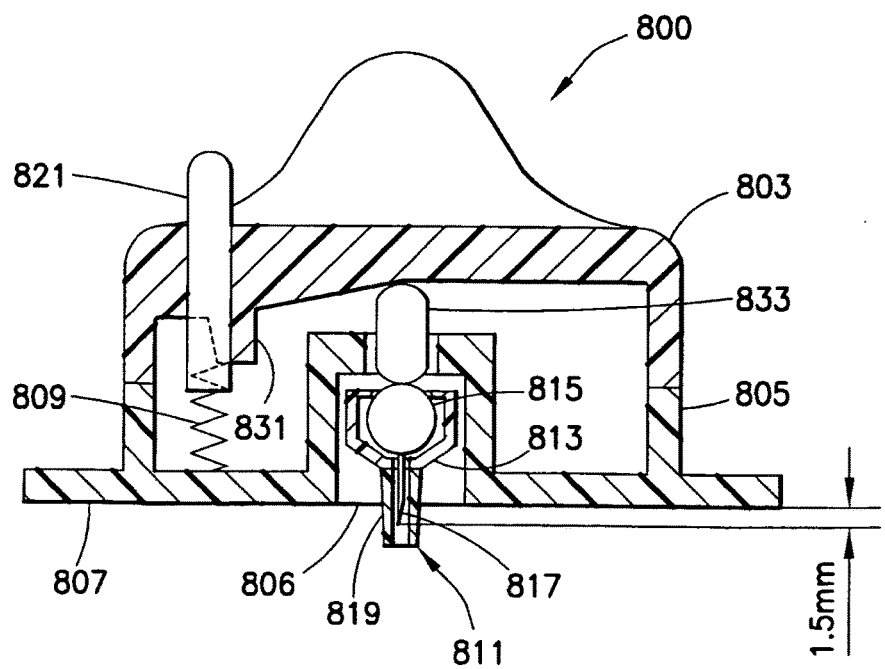
FIG. 13 is an elevational view in partial cross-section of the housing of FIG. 12 in which a medicament assembly of FIG. 10 is inserted.
Figure 14:
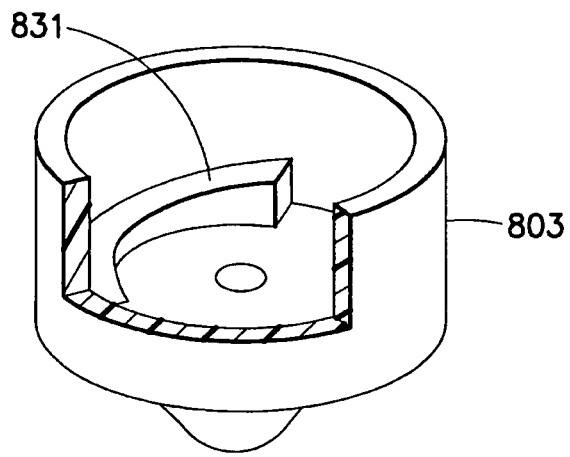
FIG. 14 is a perspective view of a cover of the housing assembly of FIG. 12.
Figure 15:
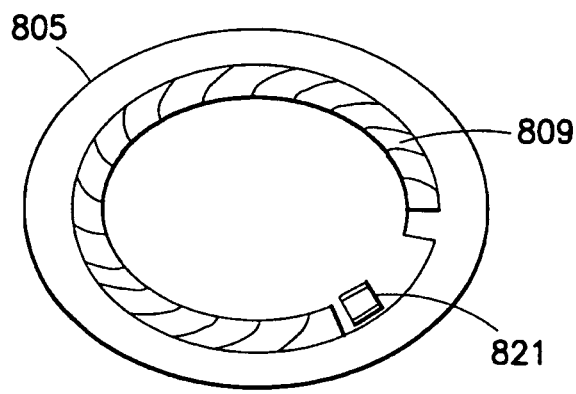
FIG. 15 is a perspective view of a base of the housing assembly of FIG. 12.
Figure 16:
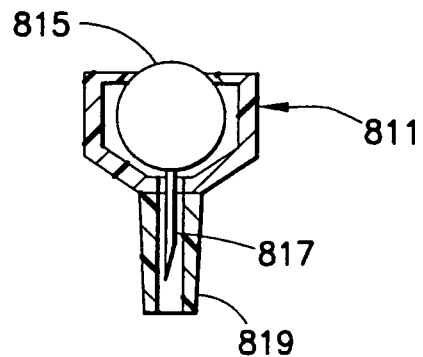
FIG. 16 is an enlarged elevational view of the hub assembly connected to the housing assembly of FIG. 12.

The cover 803 is rotatably connected to the base 805 with a spring 809. The cover 803 is rotated with respect to the base 805 until the cam release 821 latches. This rotation pre-charges the device 800 and stores energy in the spring 809. A cam 831 is formed in the cover 803, as shown in FIGS. 13 and 14. When an injection is to be made, the safety shield 819 is removed and the exposed needle 817 is inserted in a patient at a desired injection site. The cam release 821 is disengaged causing the cover 803 to rotate such that the increasing slope of the cam 831 engages a movable member 833 that is moved downwardly by the cam, thereby compressing the drug reservoir 815 and rupturing a seal in the fluid path. The medicament is then administered through the needle 817. The safety shield 819 is reconnected to the hub 813 and the hub assembly 811 is removed for disposal. A new hub assembly 811 can then be connected to the base 805 for performing another injection. Accordingly, the drug delivery device 800 is ready for use with a new hub assembly 811.

Figure 17:
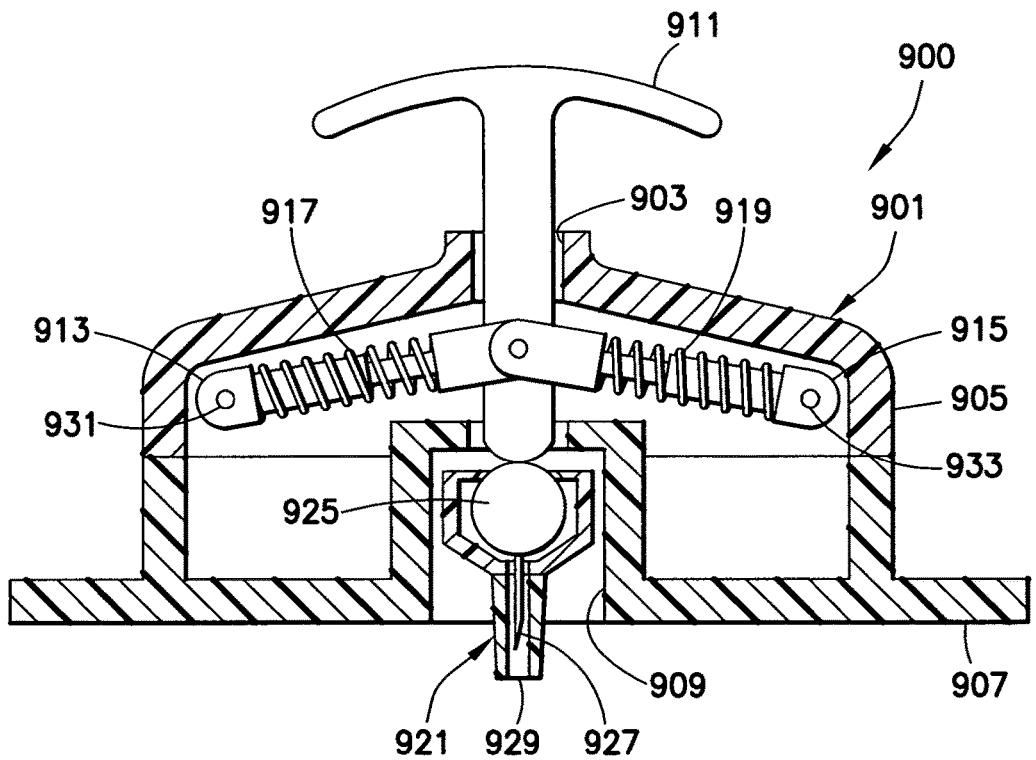
FIG. 17 is an elevational view in cross-section of a drug delivery device according to another exemplary embodiment of the present invention.
Figure 18:
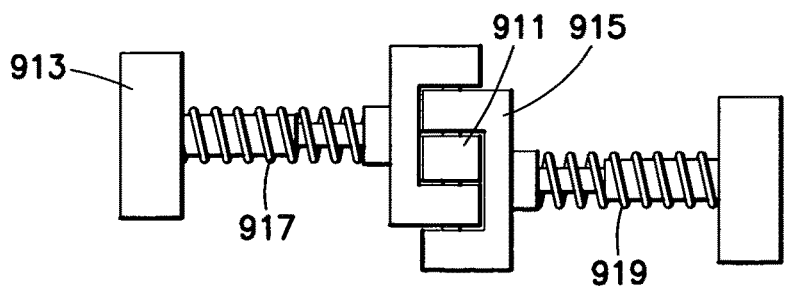
FIG. 18 is an enlarged top plan view of a linkage assembly of the drug delivery device of FIG. 17.
Figure 19:
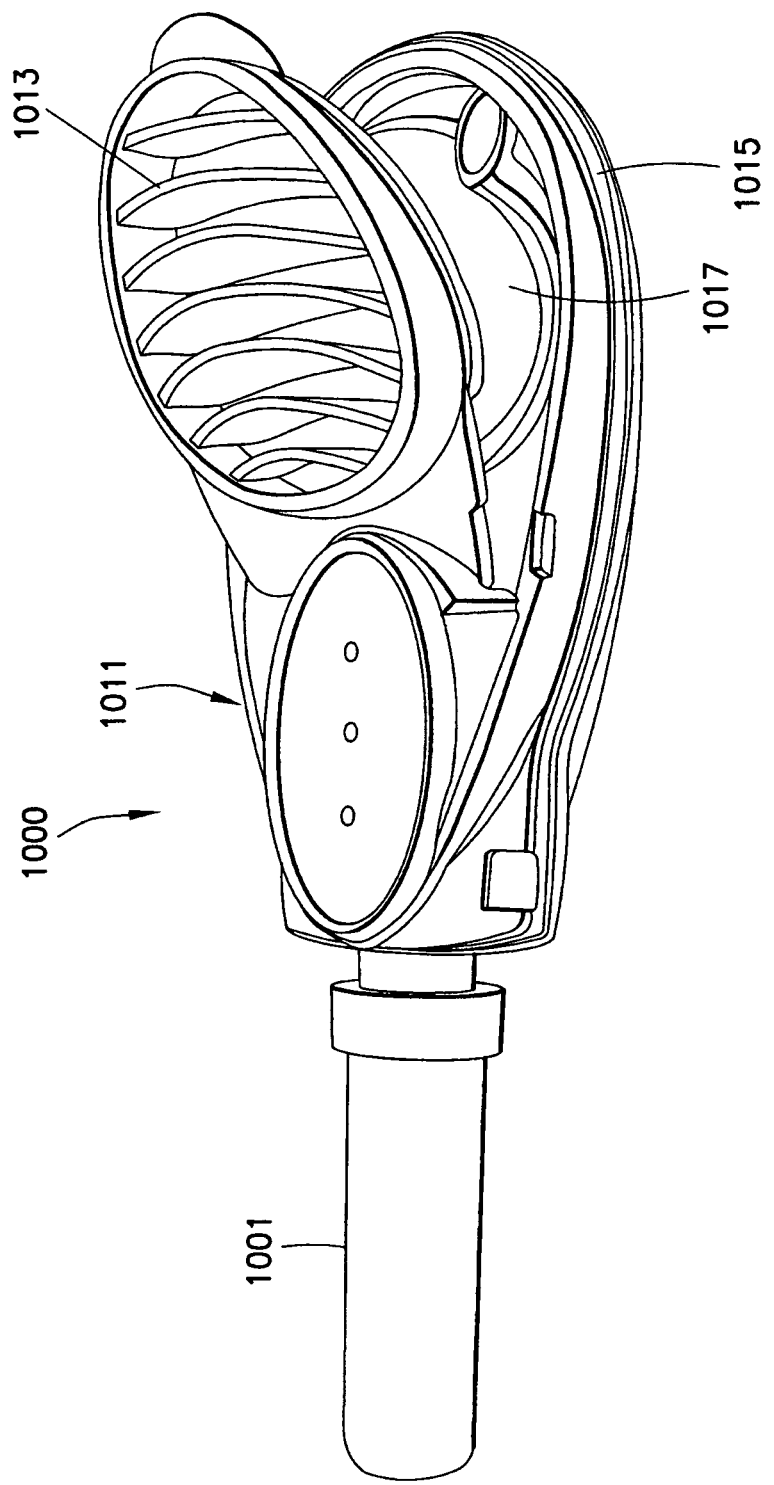
FIGS. 19-22 are perspective views of a drug delivery device according to another exemplary embodiment of the present invention.
Figure 20:
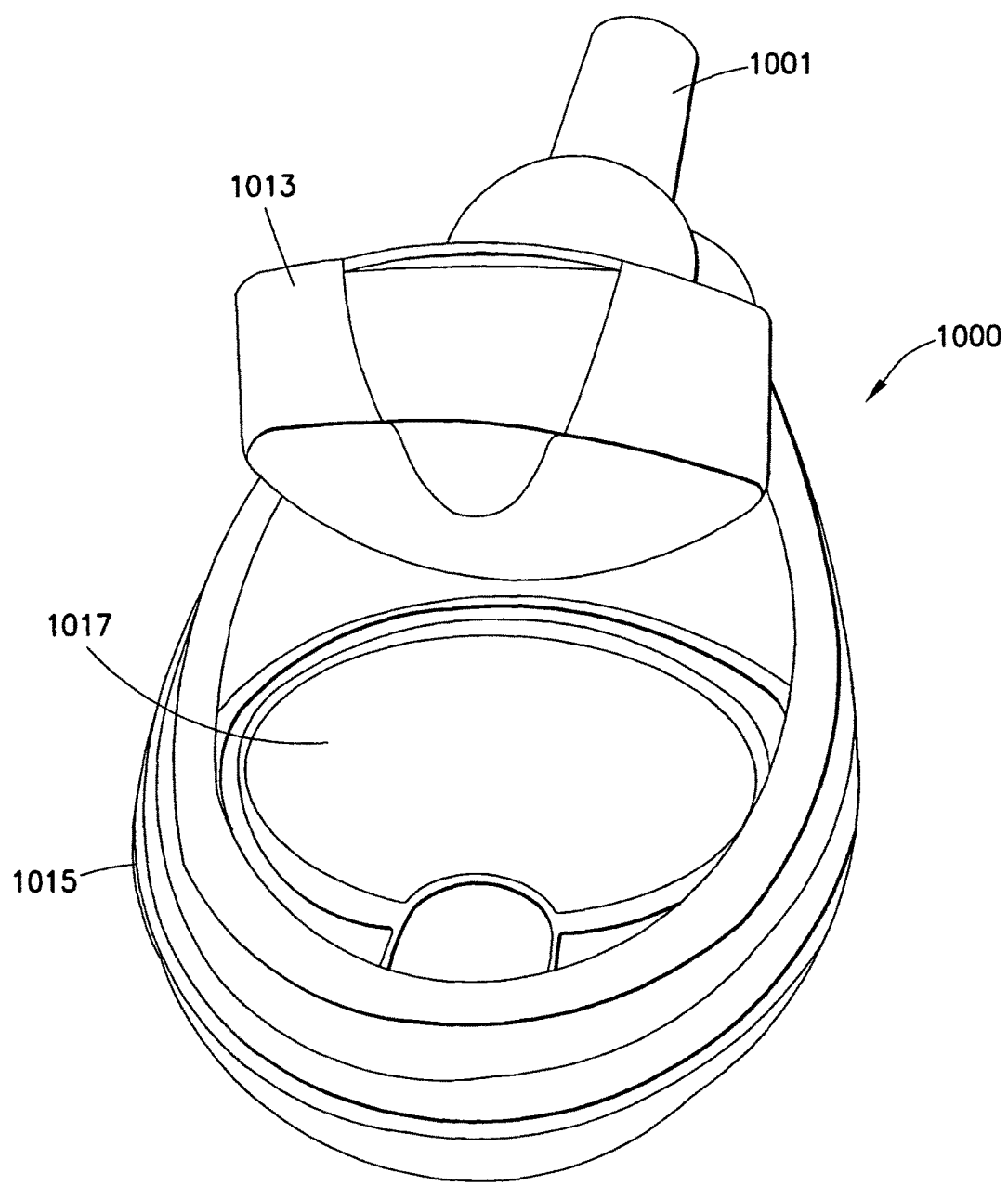
Figure 21:
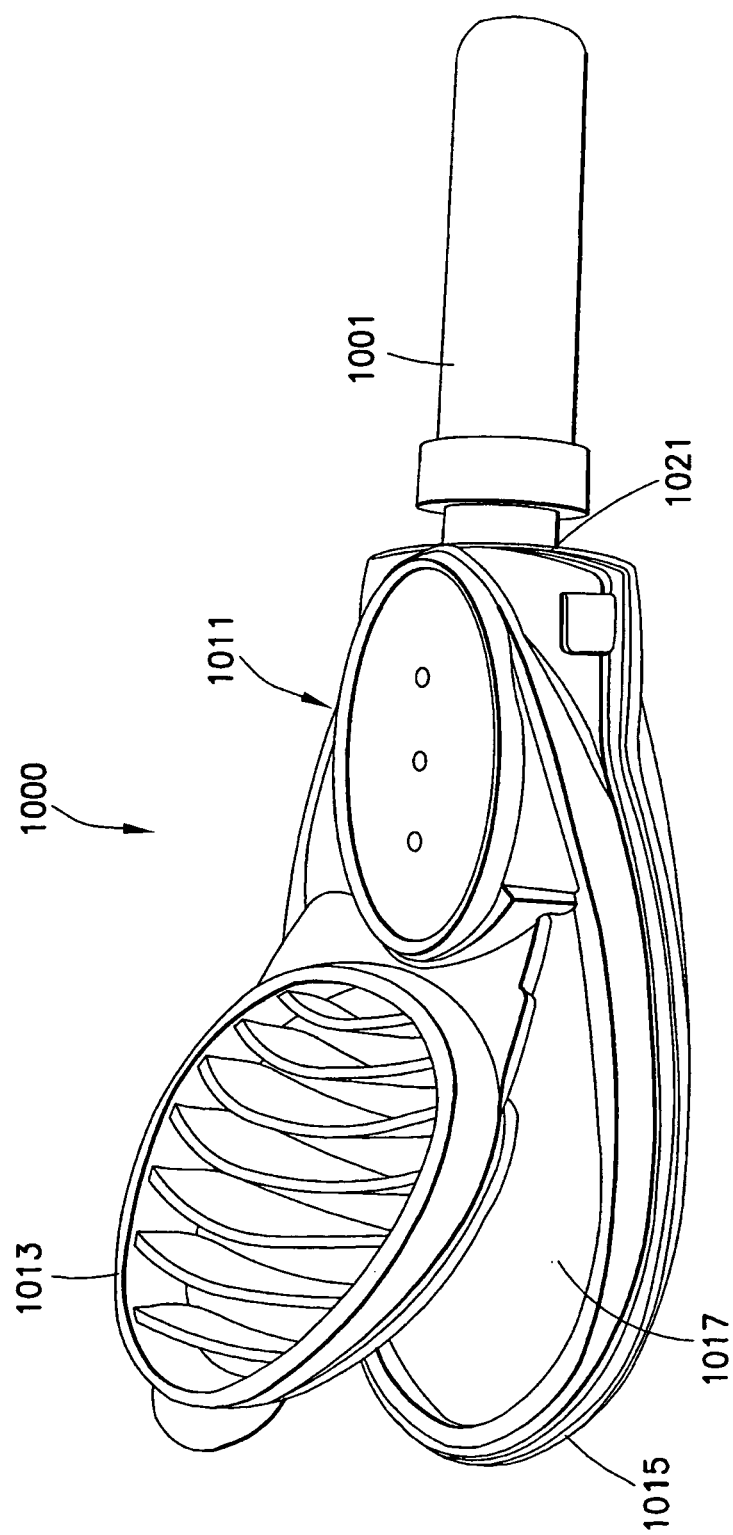
Figure 22:
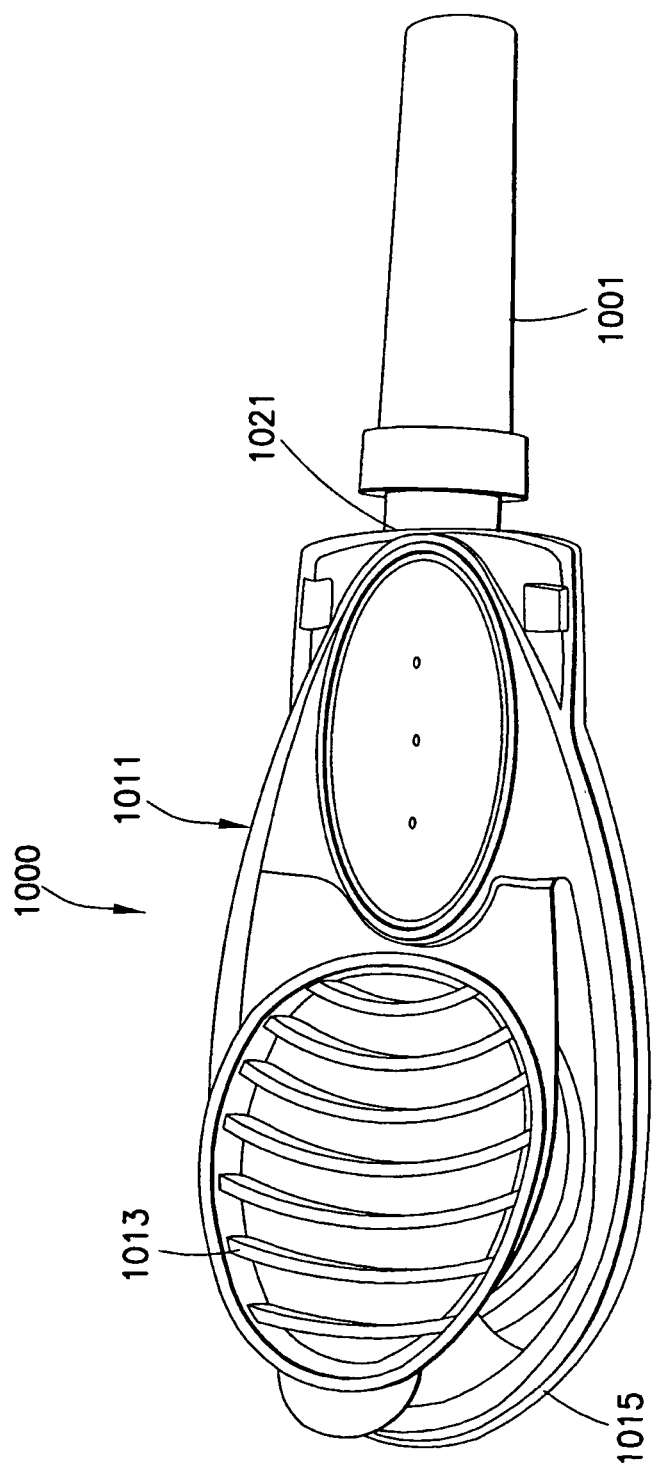

A drug delivery device 900 is shown in FIGS. 17 and 18. The drug delivery device 900 may be disposed in a housing assembly 901 substantially similar to the housing assembly 801 of FIG. 12. The drug delivery device 900 has a plunger 911 as the actuating mechanism or pressure applying member. The plunger 911 extends through an opening 903 in the cover 905 for access by the user. Two telescoping links 913 and 915 are fixed, such as by pins 931 and 933, to the cover 903.

To pre-charge the drug delivery device 900, the user holds the base 907 and retracts the plunger 911, thereby locking the plunger in the charged position. Each of the links 913 and 915 has a spring 917 and 919 to lock the plunger 911 in the charged position. A hub assembly 921 includes a hub 923, a drug reservoir 925, a needle 927 and a safety shield 929 disposed in a recess 909 in the base 907. The drug reservoir 925 is received within the hub 923. The needle 927 is secured to the hub with a non-patient end disposed to be in fluid communication with the drug reservoir 925 when a seal within the drug reservoir is ruptured. The patient end of the needle 927 is disposed externally and preferably at a depth suitable for an intradermal injection. The drug delivery device 900 is placed at the injection site, the safety shield 929 is removed, and the needle 927 is inserted in the patient's skin. Pressure is applied to the plunger 911, which overcomes the locking springs 917 and 919, thereby causing the plunger 911 to move downwardly. The downward movement of the plunger 911 compresses the drug reservoir 925 and ruptures a seal thereof, thereby administering the medicament through the needle 927 at a high pressure. The safety shield 929 is reconnected to the hub 923 and the hub assembly 921 is removed for disposal. A new hub assembly 921 can then be connected to the base 907 for performing another injection. Accordingly, the drug delivery device 900 is ready for use with a new hub assembly 921.

As shown in FIGS. 19-22, a drug delivery device 1000 is used for subcutaneous injections. A safety shield 1001 covers the needle, which has a length adapted for subcutaneous injections. A housing assembly 1011 includes an upper housing 1013 and a lower housing 1015. A drug reservoir is disposed in the cavity 1017 in the lower housing 1015. A needle connected to the lower housing 1015 by a hub 1021 is in fluid communication with the drug reservoir when a seal of the drug reservoir is ruptured. The upper housing 1013 is closed onto the lower housing, thereby compressing the drug reservoir and rupturing a seal in the fluid path. Medicament stored in the drug reservoir is forced out through the needle at a high pressure.

Figure 23:
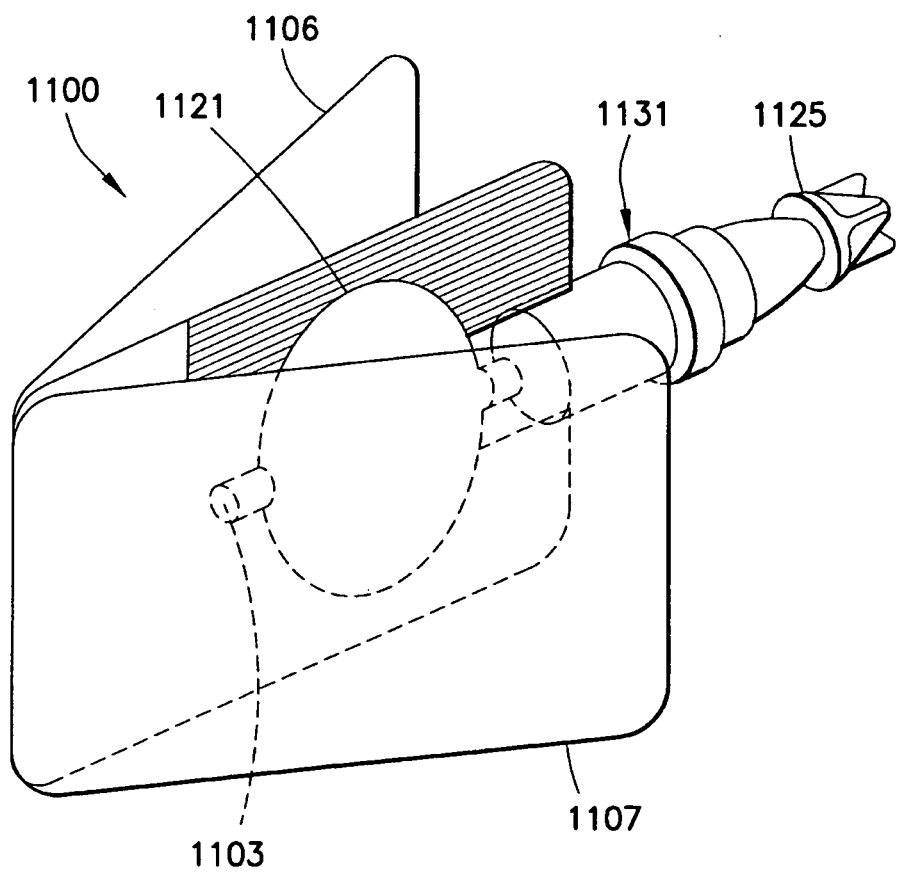
FIG. 23 is perspective view of a drug delivery device according to another exemplary embodiment of the present invention.
Figure 24:
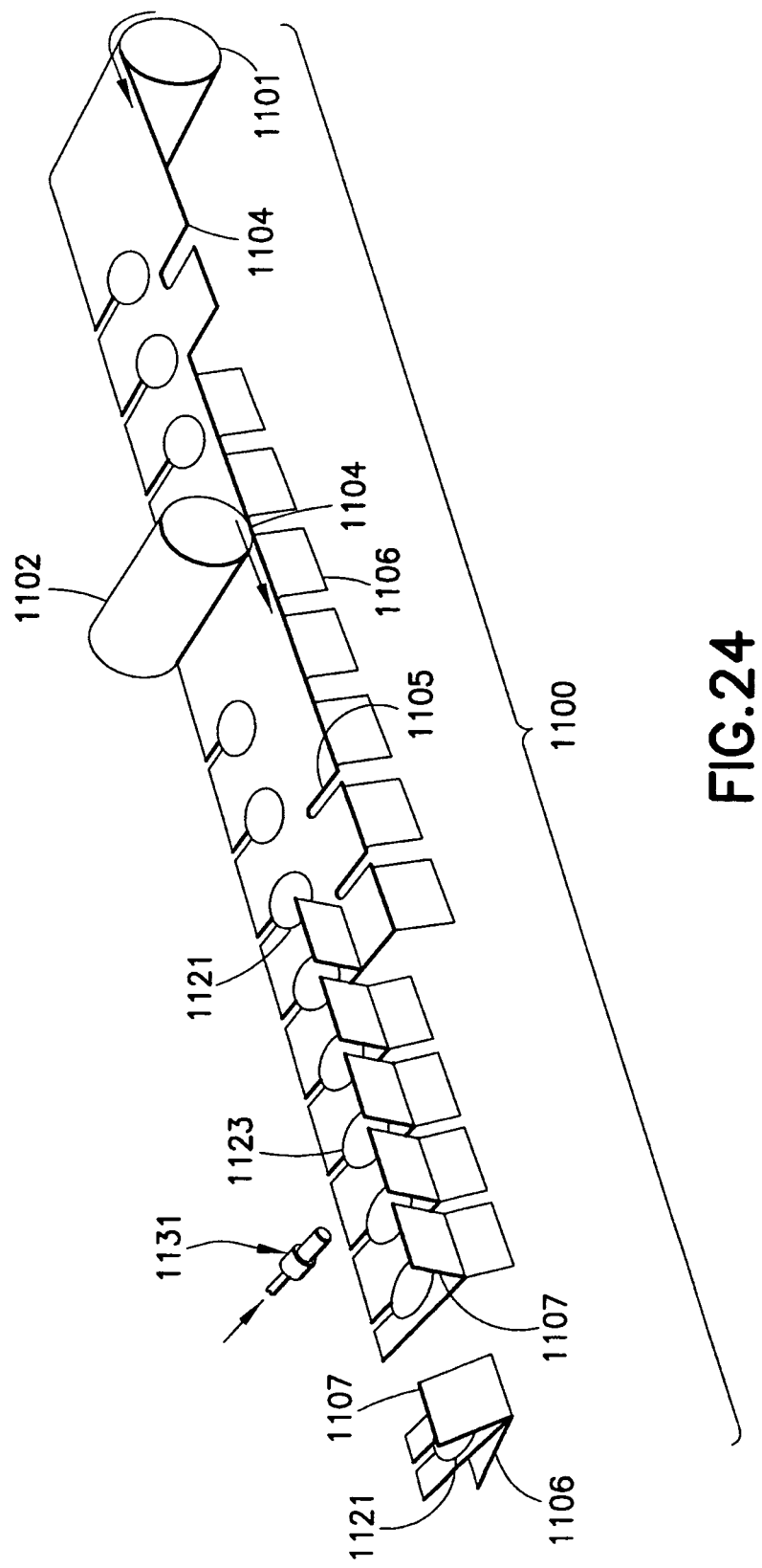
FIG. 24 is an illustration of a manufacturing process for the drug delivery device of FIG. 23.
Figure 25:
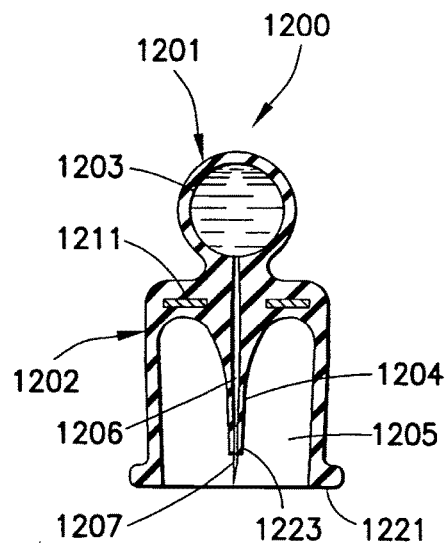
FIGS. 25-28 are elevational views in partial cross-section of a drug delivery device according to another exemplary embodiment of the present invention.

A drug delivery device 1100, as shown in FIGS. 23 and 24, is made from laminated sheets. A first laminate roll 1101 forms the bottom of the drug delivery device 1100 and a second laminate roll 1102 forms the top of the drug delivery device. A recess is formed in both the bottom and top laminate rolls, as shown in FIG. 24, by thermoforming. A notch 1104 and 1105 is formed in both the bottom and top laminate rolls to form separate levers 1106 and 1107 for each drug delivery device. The first and second laminate rolls 1101 and 1102 are merged together such that the recesses are aligned to form a drug reservoir 1121. The laminates are then bonded together to form the drug delivery device 1100. A hub assembly 1131 can then be connected to an injection channel 1123 such that the needle is in fluid communication with the drug reservoir 1121 when the drug reservoir seal is ruptured. The upper and lower levers 1106 and 1107 are folded away from one another. The drug delivery device 1100 can then be separated from the bonded laminate sheet in any suitable manner. A filling channel 1103 is formed in the drug delivery device 1100 so that medicament can fill the drug reservoir 1121. After the reservoir is filled with the medicament, the filling channel 1103 is sealed. The safety shield 1125 is removed to expose the needle. The upper and lower levers 1106 and 1107 are squeezed together to compress the drug reservoir 1121 and rupture its seal, thereby expelling the medicament with a high pressure.

A drug delivery device 1200 in FIGS. 25-28 has a first substantially ball-shaped portion 1201 and a second substantially bell-shaped portion 1202. A drug reservoir 1203 is formed in the first portion 1201 to receive a medicament. The second portion 1202 has a projection 1204 extending through a cavity 1205 thereof. A channel 1206 extends from the drug reservoir 1203 and through the entirety of the projection 1204. A needle 1207 is fixed to an open end of the channel 1206. The first and second portions 1201 and 1202 are formed of a soft, elastic material. A rigid wall 1211, such as a disk, separates the first and second portions. Preferably, an end 1221 of the second portion 1202 extends below an end 1223 of the projection 1204.

Figure 26:
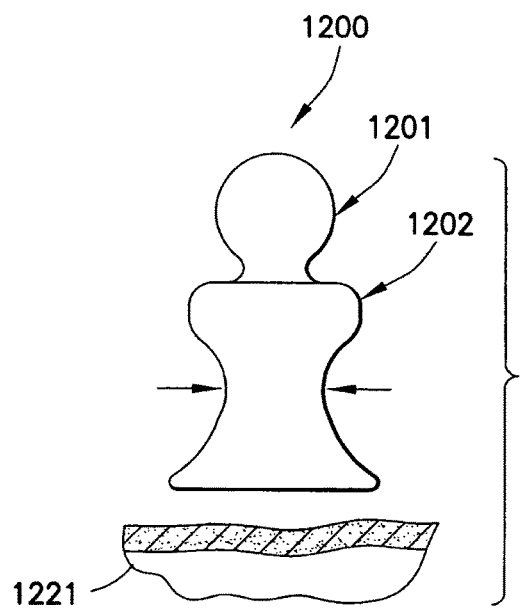
Figure 27:
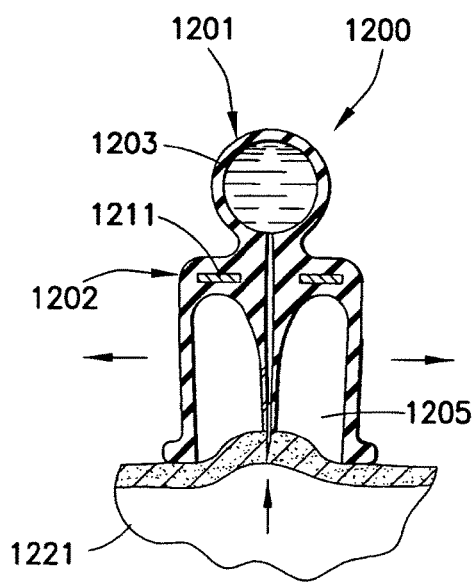
Figure 28:
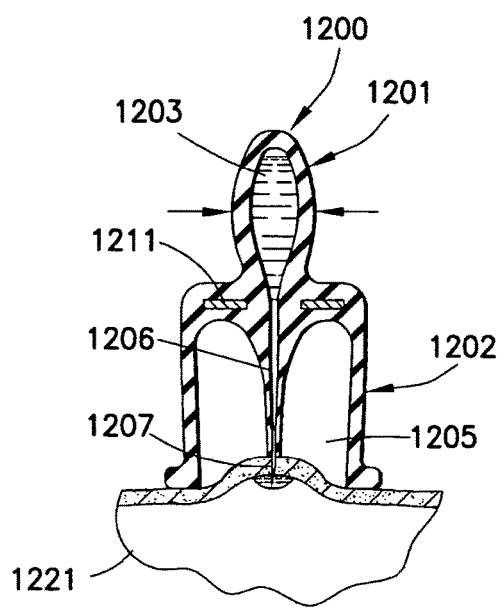

When an injection is to be made, the user squeezes the second portion 1202 of the drug delivery device 1200, as shown in FIG. 26, prior to placing the device on the skin 1221. The device 1200 is then placed on the skin 1221 and the second portion 1202 is released such that the elasticity thereof reestablishes the original bell-shape of the device, thereby creating a vacuum in the cavity 1205, as shown in FIG. 27. The vacuum sucks the skin 1221 at the injection site upwardly into the cavity 1205, thereby piercing the skin with the needle 1207. The medicament is then administered to the patient by squeezing the first portion 1201, which expels the medicament through the channel 1206 and needle 1207 and into the injection site, as shown in FIG. 28. The drug delivery device 1200 is then removed from the injection site and properly disposed of.

The drug delivery device according to exemplary embodiments of the present invention may include a self-priming feature. The drug reservoir may be made of a material with elastic properties such that the reservoir may be slightly overfilled with the medicament. Upon activation (connection of the hub assembly to the drug reservoir), the pressure inside the reservoir dispenses a small amount of the medicament through the needle, thereby priming the drug delivery device.

The drug delivery device may be capable of administering multiple doses in a cartridge-like device contained inside a pen or other suitable packaging. Such a drug delivery device could have multiple doses encapsulated within a single disposable plastic wheel, as shown in FIG. 10, or in a rotary cartridge or turret configuration. Alternatively, the drug delivery device may have one reusable needle and three or more drug reservoirs (one for each meal) encapsulated within a laminated film.

Additionally, the drug delivery device may have a longer needle suitable for subcutaneous injections, as shown in FIGS. 19-22.

Furthermore, the drug delivery device may be adapted to be used with an insulin pump or a drug infusion set with two needles (one for subcutaneous infusion and one for intradermal injection). The intradermal needle is used to replicate the first-phase insulin produced by a healthy pancreas, and the subcutaneous needle is used for basal dosing and for the normal mealtime bolus doses of insulin.

Still furthermore, the drug delivery device may be a disposable pen-like device that delivers multiple first-phase replacement insulin doses of a fixed size.

As noted above, a seal 141 (FIGS. 1 and 2) can be disposed in the drug reservoir. Alternatively, a semi-rigid foam is disposed inside a needle cap to act as a sterile barrier.

It is within the scope of the present invention to utilize existing types of single-use disposable syringes, such as that disclosed in the aforementioned U.S. Pat. No. 4,955,871 to Thomas, which is incorporated herein by reference in its entirety, to provide first-phase replacement insulin doses by prefilling them with a limited quantity of insulin in the range of approximately 1 to 15 units of U-100 insulin (10 to 150 microliters) and administering the first-phase replacement insulin doses subcutaneously or intradermally, with or without force multiplication. Any suitable type of insulin or insulin analog may be used, such as fast-acting insulin.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A drug delivery device for administering a low dose of a medicament, comprising:
    a housing having a needle hub with a fluid outlet channel;
    a drug reservoir disposed in said housing and containing a medicament, said drug reservoir having a seal formed from a layer that is ruptured by applying a dispensing pressure to said drug reservoir, said drug reservoir having an outlet passage extending between said seal and said fluid outlet channel in said needle hub;
    a needle connected to said housing and having a first end in communication with said drug reservoir and a second end extending outwardly from said needle hub, said fluid outlet channel communicating with said drug reservoir, and said needle having an end received in said outlet passage of said drug reservoir and spaced from said seal; and
    a pressure applying member movably connected to said housing and movable between first and second positions with respect to said drug reservoir, said pressure applying member not applying pressure to said drug reservoir in said first position and contacting and applying the dispensing pressure to said drug reservoir in said second position rupturing said seal and dispensing said medicament stored in said drug reservoir through said needle, said first end of said needle being spaced from said seal of said drug reservoir defining a gap between said needle and said seal of said drug reservoir when said pressure applying member is in said first position and said needle being spaced from said seal of said drug reservoir defining the gap between said needle and seal of said drug reservoir when said pressure applying member is in said second position.

2. The drug delivery device according to claim 1, wherein said drug reservoir has a volume of between 1 and 15 units.

3. The drug delivery device according to claim 1, wherein said medicament is insulin.

4. The drug delivery device according to claim 1, wherein said pressure applying member moves in a direction substantially perpendicular to a longitudinal axis of said needle.

5. The drug delivery device according to claim 1, wherein said pressure applying member comprises a piston.

6. The delivery device of claim 1, wherein
    said housing has a first piston oriented for contacting said drug reservoir and extending from a wall of said housing, and
    said pressure applying member has a second piston opposing said first piston for applying the dispensing pressure toward said first piston.

7. The drug delivery device of claim 1, wherein
    said dispensing pressure ruptures said seal and dispenses said medicament through said outlet passage to said needle.

* * * * *